United States Patent [19]

Ikeda et al.

[11] Patent Number: 5,576,007
[45] Date of Patent: Nov. 19, 1996

[54] ZEOLITE INSECTICIDE FOR TERMITES

[75] Inventors: Satoshi Ikeda; Yoshiki Inoue; Naoaki Yamamoto, all of Takamatsu, Japan

[73] Assignee: Kabushiki Kaisha Shikoku Sogo Kenkyusho, Kagawa-ken, Japan

[21] Appl. No.: 78,169

[22] PCT Filed: Oct. 21, 1992

[86] PCT No.: PCT/JP92/01364

§ 371 Date: Oct. 21, 1993

§ 102(e) Date: Oct. 21, 1993

[87] PCT Pub. No.: WO93/07752

PCT Pub. Date: Apr. 29, 1993

[30] Foreign Application Priority Data

Oct. 21, 1991 [JP] Japan .................................. 3-272311
Sep. 4, 1992 [JP] Japan .................................. 4-237276

[51] Int. Cl.$^6$ ................................................. A01N 25/34
[52] U.S. Cl. ........................... 424/408; 424/403; 424/405; 424/409
[58] Field of Search .................... 424/404, 405, 424/409, 684, 724

[56] References Cited

U.S. PATENT DOCUMENTS

| | | | |
|---|---|---|---|
| 3,124,505 | 3/1964 | Doyle et al. | 424/724 |
| 3,235,451 | 2/1966 | Odeneal | 424/724 |
| 4,279,895 | 7/1981 | Carle | 424/724 |
| 4,906,464 | 3/1990 | Yamamoto et al. | 424/78 |
| 4,938,958 | 7/1990 | Niira et al. | 424/79 |
| 4,984,663 | 1/1991 | Kato . | |
| 5,165,934 | 11/1992 | Wada et al. | 424/409 |
| 5,180,585 | 1/1993 | Jacobson et al. | 424/405 |
| 5,186,935 | 2/1993 | Tucker | 424/410 |
| 5,204,119 | 4/1993 | Shiobara et al. | 424/489 |
| 5,264,225 | 11/1993 | Varga et al. | 424/684 |
| 5,298,252 | 3/1994 | Hagiwara et al. | 424/409 |

FOREIGN PATENT DOCUMENTS

| | | |
|---|---|---|
| 64-25705 | 1/1989 | Japan . |
| 64-19011 | 1/1989 | Japan . |
| 64-25703 | 1/1989 | Japan . |

*Primary Examiner*—Thurman K. Page
*Assistant Examiner*—William E. Benston, Jr.
*Attorney, Agent, or Firm*—Keck, Mahin & Cate

[57] ABSTRACT

The insecticide has little adverse effect on man or animals and presents little risk of environmental pollution, but eliminates harmful insects, such as termites, even when used over long periods of time without the insects acquiring resistance. The insecticide contains powdered zeolite, some of the particles of powdered zeolite having a diameter smaller than the distance between the body hairs of the insect which is to be killed.

6 Claims, 12 Drawing Sheets

ZEOLITE INSECTICIDE FOR TERMITES

FIELD OF APPLICATION

This invention relates to an insecticide.

BACKGROUND OF INVENTION

In order to eliminate termites, cheyletids (cheyletidae) and other harmful insects, chemical insecticides are generally used. To eliminate termites or cheyletids, for example, chemical insecticides having a strong acute toxicity such as organic phosphorus compounds or pyrethroid compounds are widely employed.

PROBLEMS WHICH THIS INVENTION ATTEMPTS TO SOLVE

Although these types of chemical Insecticides eliminate harmful insects due to the effect of their chemical components, however, they often have an adverse effect on man and animals. It is therefore feared that the spraying of such chemical substances having strong acute toxicity will lead to environmental pollution.

Further, insects gradually acquire a resistance to chemical insecticides as a result of repeated exposure to them. A chemical insecticide which was initially effective may thus subsequently lose all of its activity.

SUMMARY OF THE INVENTION

This invention was conceived to resolve the aforesaid problems. It aims to provide an insecticide which has little adverse effect on man or animals and presents little risk of environmental pollution, but which definitively eliminates harmful insects even when used over long periods of time without the insects acquiring resistance.

In order to achieve the above objectives, the invention provides an insecticide containing powdered zeolite, characterized in that this powdered zeolite comprises particles having a diameter smaller than the distance between body hairs on the insects it is desired to eliminate.

In the insecticide provided, the zeolite has moisture regulating properties, and can therefore maintain dry conditions unsuitable for sustaining harmful insects in areas where the insecticide is used.

In areas to which this insecticide is applied, therefore, harmful insects are not easily sustained, the number of harmful insects decreases, and even if some harmful insects still remain, they are far less active.

As the aforesaid zeolite contains some particles having a diameter smaller than the distance between insect body hairs, a fine powder of these particles adheres to the insect's body surface despite the presence of the hairs. This prevents release of carbon dioxide gas from the insect's skin, and causes the insect's death due to respiratory failure.

If the harmful insect which it is desired to eliminate has stomata, the aforesaid fine zeolite powder adheres to the stomata. This prevents the insect from taking in oxygen, and causes the insect's death due to oxygen deficiency.

Further, when foreign matter adheres to an insect's the body surface or hairs, the insect tries to brush it off. In this brushing off action, the insect scratches itself. The aforesaid fine powder then adheres to the scratches despite the presence of body hairs, and due to the moisture regulating properties of the zeolite, the zeolite absorbs the insect's body fluids which causes the insect's death by dehydration.

This type of zeolite is not only less toxic than conventional insecticides, but is also effective as an insecticide due to the aforesaid mechanisms.

The insecticide provided by the invention therefore has little adverse effect on man or animals and presents little risk of environmental pollution, but definitively eliminates harmful insects even when used over long periods of time without the insects acquiring resistance.

DETAILED DESCRIPTION OF THE INVENTION

This invention will now be described in further detail with reference to the drawings. First, the insecticidal action of zeolite will be described.

According to studies performed by the inventors, the physical insecticidal action of zeolite appears to be due to a combination of the following three mechanisms.

The first mechanism will be described with reference to FIG. 1.

Figure 1:
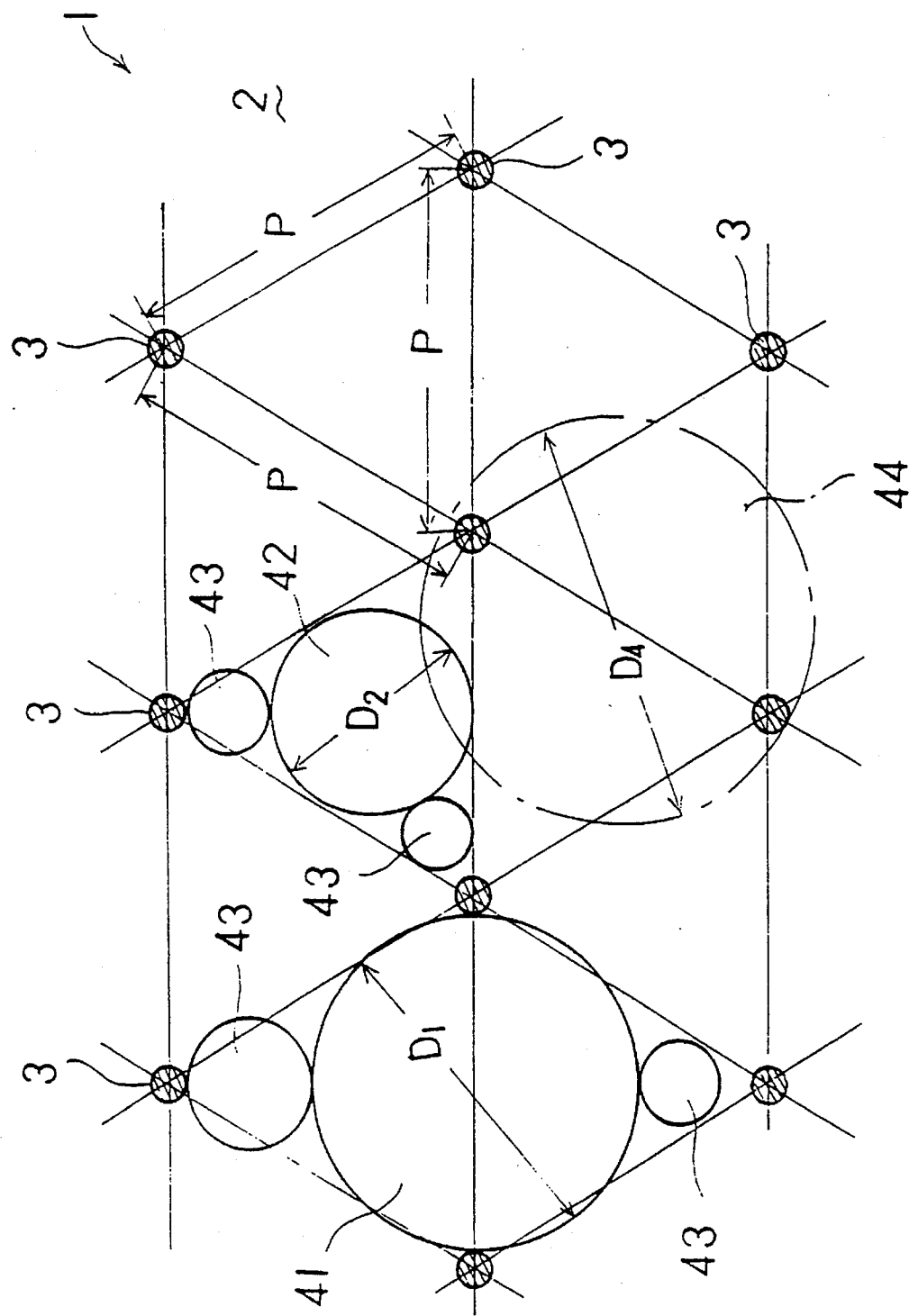
FIG. 1 is a schematic diagram illustrating the first mechanism according to which harmful insects are eliminated by the insecticide of the present invention.
Figure 2:
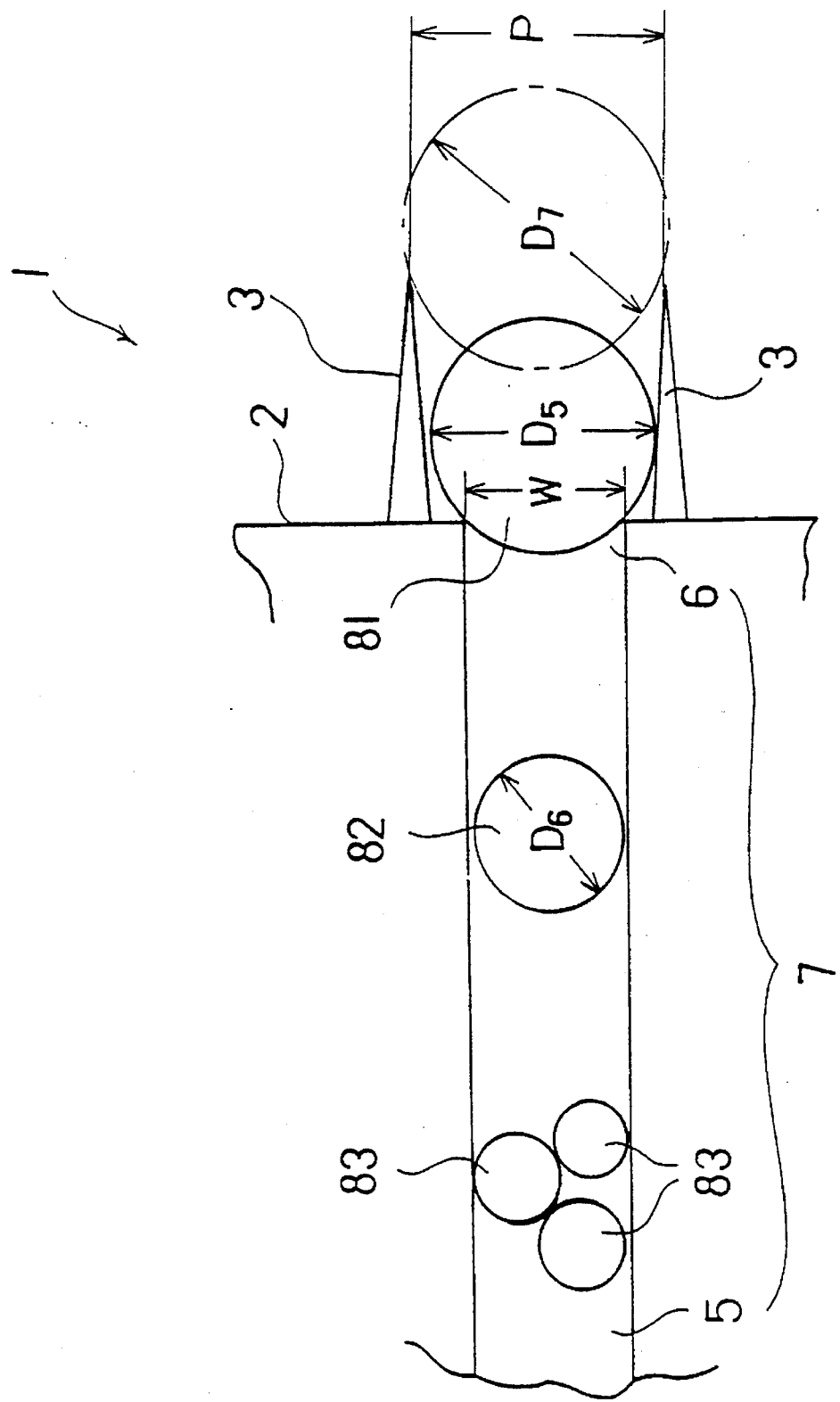
FIG. 2 is a schematic diagram illustrating the second mechanism according to which harmful insects are eliminated by the insecticide of the present invention.

FIG. 1 is a flat schematic representation of an insect's body. 1 is the insect, 2 is the skin of the insect's body surface, 3 are insect body hairs, and 41, 42, 43 and 44 are particles of an insecticide consisting of powdered zeolite.

The insect 1 takes oxygen into its body through stomata or the skin 2, and expels carbon dioxide gas directly through the skin 2.

The skin 2 through which the insect expels carbon dioxide has a pattern of numerous body hairs 3.

These body hairs 3 are formed at predetermined positions according to the species of the insect 1. The arrangement of hairs 3 on the skin 2 of the insect 1 is represented schematically for various types of insect as shown in FIG. 1, and although in practice the distances between these hairs 3 may not all be identical, it will be assumed for the sake of convenience that the distance between hairs is a constant P.

Further, the shapes of the insecticide particles 41, 42, 43 and 44 will in practice be different. To simplify the following explanation of mechanisms, however, they are represented as circles of different diameter in the drawings.

The ways in which these particles 41, 42, 43 and 44 adhere to the insect's skin 2 and hairs 3 is as follows.

The diameter D1 of the particle 41 is slightly smaller but effectively the same as the distance P between the hairs 3.

The particle 41 is therefore able to reach the skin 2 of the insect 1 through the spaces between the hairs 3.

After reaching the skin 2, the particle 41 adheres to the skin 2 due to the presence of oil or moisture on the skin.

Release of carbon dioxide gas from the area of the skin 2 covered by the insecticide particle 41 is thereby prevented. Moreover, if the insect is a species that takes in oxygen through the skin 2, this particle 41 also prevents oxygen intake through the skin 2 at this position.

The diameter D2 of the insecticide particle 42 is smaller than that of the particle 41, and the diameter D3 of the insecticide particle 43 is still smaller than that of the particle 42.

As is clear from FIG. 1, therefore, the insecticide particles 42 and 43 which have a smaller diameter than that of the particle 41, can also reach the skin 2 of the insect 1 without being obstructed by the body hairs 3, and they adhere to the skin 2 in the same way as the particle 41 so as to prevent release of carbon dioxide gas.

In this invention, the case of the particle 44 is given as a comparative example. The diameter D4 of this particle 44 is greater than the distance P between the body hairs 3, and as can be seen from FIG. 1, some of the hairs 3 prevent the particle 44 from adhering to the skin 2. Consequently, it cannot prevent release of carbon dioxide gas from the skin 2 of the insect 1 in the same way as the aforesaid particles 41, 42 and 43.

When release of carbon dioxide from the skin 2 is prevented by the particles 41, 42 and 43, the decrease of respiratory function of the insect 1 approximately depends on the area which is covered by these particles. If this area exceeds a certain upper limit, the insect's respiration fails and the insect 1 finally dies.

In using this type of insecticide to eliminate insects, therefore, it is extremely important to maximize the area of the skin 2 to which the particles 41, 42 and 43 adhere. Maximization of this surface area and elimination of the insects can thus be achieved by suitably choosing the particle diameter of the insecticide according to the type of insect.

Next, the second mechanism will be described with reference to FIG. 2. This second mechanism is limited to the case where the insect to be eliminated has stomata.

FIG. 2 is a schematic view in section of the stomata of the insect. 1 is the insect having stomata, 2 is the skin of the insect's body, and 3 are the insect's hairs.

In the insect 1 having stomata, an air tube 5 extending from the insect's body opens out on the skin 2 so as to form a stoma 6. These air tubes 5 and stomata 6 constitute the insect's respiratory system. The respiratory system 7 functions as a network of passages for taking oxygen into the insect's body.

In such an insect having a stoma 6, let the distance between body hairs 3 near the stoma 6 be P, and the opening (diameter) of the stoma be W.

In FIG. 2, 81, 82, 83 and 84 are insecticide particles consisting of powdered zeolite. The shapes of the insecticide particles 81, 82, 83 and 84 will in practice be different, but to simplify the following explanation of mechanisms, they are represented as circles of different diameter in the drawings.

The actions of the particles 81, 82, 83 and 84 in the vicinity of the stoma 6 of the insect 1 differ according to their diameters. In the following description, the particles 81, 82 and 83 function as active components, the case of the particle 84 being given as a comparative example.

The diameter D5 of the particle 81 is smaller than the distance P between the body hairs 3, and larger than the opening W of the stoma 6.

The particle 81 reaches the skin 2 of the insect 1 through the hairs 3, and is deposited on the surface of the stoma 6. This particle 81 adheres to the skin 2 due to the presence of oil or water on the skin. The stoma 6 is therefore covered and blocked by the particle 81, and oxygen intake through the stoma 6 is prevented.

The diameter D6 of the particle 82 is a little smaller the distance P between the hairs 3 and the opening W of the stoma 6.

The particle 82 therefore reaches the skin 2 of the insect 1 in the same way as the particle 81, and it may also penetrate the air tube 5 through the stoma 6.

If the particle 82 enters the air tube 5, the effective area of the air tube 5 is largely reduced. The insect's oxygen intake is therefore impaired, and as the particle 82 does not easily fall out of the air tube 5, the insect 1 will eventually die due to long-term oxygen deficiency.

In the case of the particle 83, which has a diameter even smaller than that of the particle 82, the hairs 3 offer practically no obstacle to the particle reaching the skin 2 of the insect 1, and as moreover the stoma 6 is considerably larger than the particle 83, there is a high probability that the particle 83 will penetrate the air tube 5.

The particle 83 has a comparatively higher probability of penetrating the air tube 5 through the stoma 6. Whereas it would be difficult for a single particle such as the particle 82 to block the air tube 5, therefore, a plurality of the particles 83 can build up in the air tube 5 so as to reduce its effective cross-sectional area, and the insect 1 dies due to oxygen deficiency.

The particle 84 is given as a comparative example in the case of the same insect 1, its diameter D7 being larger than the distance P between the hairs 3.

The particle 84 cannot reach the skin 2 of the insect 1 due to obstruction by the hairs 3, hence it cannot be expected to block the stoma 6. As the distance P between the hairs 3 and the opening W of the stoma 6 differ according to the type of insect, however, this particle 84 may in some cases have an effect which is comparable to that of the particles 81 to 83.

The insecticide particles 81, 82 and 83 therefore adhere to the respiratory system 7, prevent oxygen intake through the stomata 6, and cause the death of the insect 1 due to oxygen deficiency, thereby achieving the objective of eliminating it.

Next, the third mechanism will be described with reference FIG. 3. This third mechanism is a physical mechanism of eliminating harmful insects using the moisture regulating property of zeolite.

Zeolite exists as either natural zeolite or artificial zeolite. In general, both types have a large ion exchange capacity of the order of 50 meq/100 g, and have moisture regulating or absorption properties required for the third mechanism.

In general, if a particle of foreign matter comes to adhere to the skin 2 or the body hairs 3 of the insect 1, the insect 1 tries to brush off the particle. This causes a scratch 11 on the skin 2 of the insect 1, and insect body fluids ooze out from the scratch.

If an insecticide 12 consisting of the aforesaid zeolite is brought into contact with the scratch 11, the body fluids of the insect 1 are absorbed by the zeolite due to its moisture regulating or absorption properties, and the insect 1 therefore dies due to dehydration.

In order for this mechanism to be effective, the zeolite must reach the scratch 11 on the skin 2. As described hereintofore, however, there are usually hairs 3 on the skin 2 of the insect 1 which prevent the aforesaid insecticide 12 from coming into contact with it. It is therefore important to enable the insecticide 12 to avoid the obstruction presented by these hairs 3 so that it reaches the scratch 11 on the skin 2.

For this purpose, the zeolite is used in powder form. By making the particle diameter D8 of the insecticide 12, which consists of powdered zeolite, smaller than the distance P between the body hairs 3 of the insect 1, the probability that the insecticide 12 will come into contact with the scratch 11 is increased, and the death of the insect can be ensured.

Figure 3:
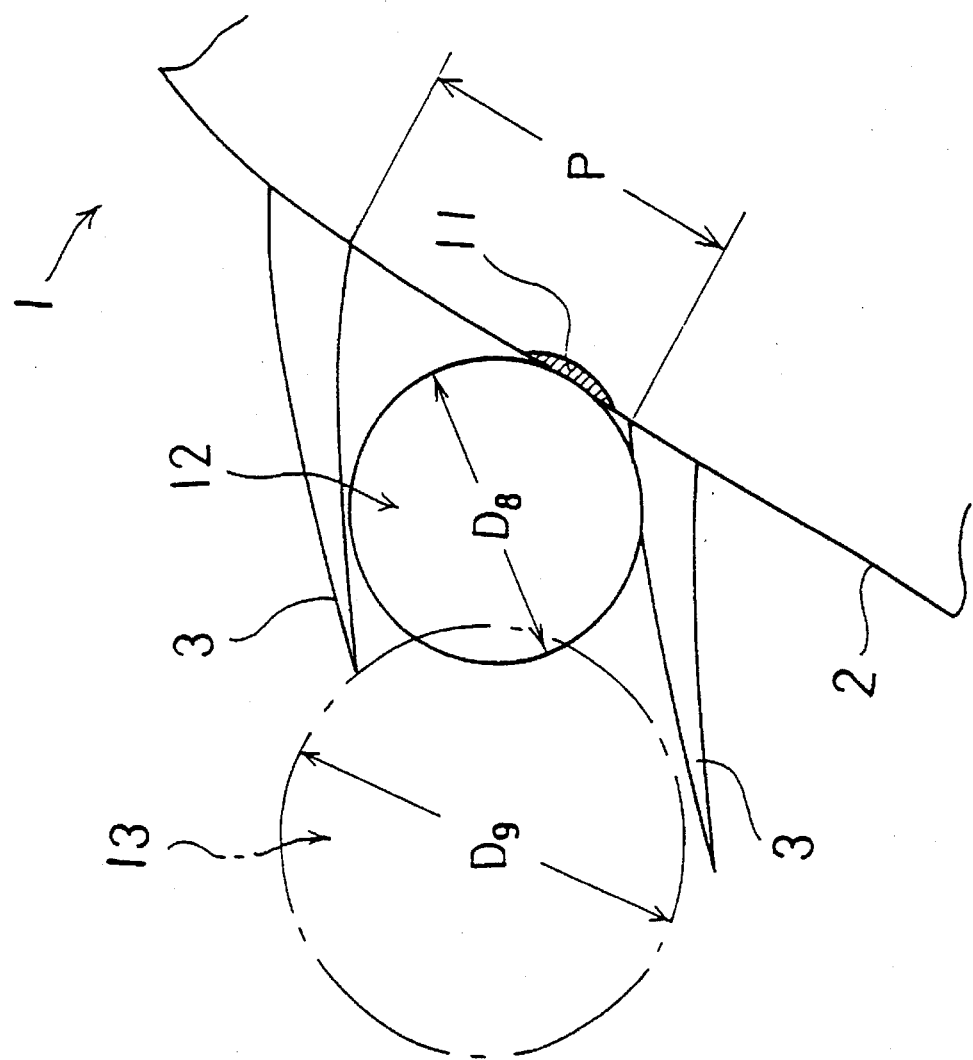
FIG. 3 is a schematic diagram illustrating the third mechanism according to which harmful insects are eliminated by the insecticide of the present invention.

FIG. 3 also shows that in the case of an insecticide 13 having a particle diameter D9 larger than the distance P between the aforesaid body hairs 3, the insecticide is prevented from reaching the scratch 11 by the hairs 3. In FIG. 3, to facilitate understanding of the third mechanism, the particles of the insecticides 12 and 13 are represented simply as spheres, although in practice they will have many different shapes.

The common advantage of the first, second and third mechanisms by which powdered zeolite acts is that unlike the case of conventional chemical insecticides, harmful insects can be eliminated from an area without spraying high concentrations of chemicals having high acute toxicity in the area. The adverse effects of chemical insecticides on man, animals and the environment can therefore be avoided, and as use is made of the physical properties of powdered solids, harmful insects can be eliminated even when the insecticides are used over long periods of time without the insects acquiring resistance.

The insecticidal properties of zeolite, which are thought to be due to a combination of the first, second and third mechanisms described hereintofore, were confirmed by the following confirmatory tests.

In these tests, a filter paper was placed in the bottom of a Petri dish. A powdered insecticide was uniformly spread on this filter paper, 10 insects were placed in the dish, and the behavior of the insects was observed over a period of time.

The Petri dishes used in this test had a diameter of 9 cm. The test was performed with 0.64 g of the aforesaid insecticide (corresponding to 100 g/m$^2$), the test insect being the worker of Formosan subterranean termite.

In this case, the aforementioned distance P between the body hairs of the insect 1 is 63 μm, and the opening W of the stomata is of the order of 30 μm.

Confirmatory tests of the properties of the insecticides of Examples 1 and 2 consisting of only natural zeolite will first be described.

The insecticides of the first and second examples, were obtained by crushing zeolite rock, which is a naturally occurring aluminosilicate ore, to a fine powder.

The natural zeolite used in Example 1 was Izukalite (commercial name) manufactured by Izumo Chemicals Ltd., and that used in Example 2 was Zeofoil (commercial name) manufactured by Shin Tohoku Chemicals Ltd.

Table 1 shows the chemical compositions (wt %) of these natural zeolites used in Examples 1 and 2. Table 1 also shows the chemical composition of the synthetic zeolite of Example 3.

TABLE 1

| Chemical component | Example 1 | Example 2 | Example 3 |
|---|---|---|---|
| $SiO_2$ | 70.17 | 72.15 | 48.25 |
| $Al_2O_3$ | 12.15 | 13.75 | 21.52 |
| $Fe_2O_3$ | 1.14 | 0.20 | — |
| MnO | 0.06 | — | — |
| CaO | 1.88 | 3.26 | 5.22 |
| MgO | 0.33 | — | — |
| $Na_2O$ | 1.95 | 1.86 | 7.52 |
| $K_2O$ | 2.34 | 1.66 | 1.06 |
| $TiO_2$ | 0.17 | — | — |
| $H_2O$ | — | 6.63 | 7.12 |
| $P_2O_5$ | — | — | — |
| Others | — | 0.49 | Fe:3.25 |

After the zeolites having these chemical compositions were crushed by a crusher such as that known in the art, particle classification was performed so as to obtain the insecticides of Examples 1 and 2.

The ion exchange capacity of the insecticides of Examples 1 and 2 was measured according to the Zeolite Testing Method of the Japanese Soil Hardness Ordinances.

In Example 1, this capacity was 130 to 160 meq/100 g, and in Example 2, it was 150 to 170 meq/100 g.

Figure 4:
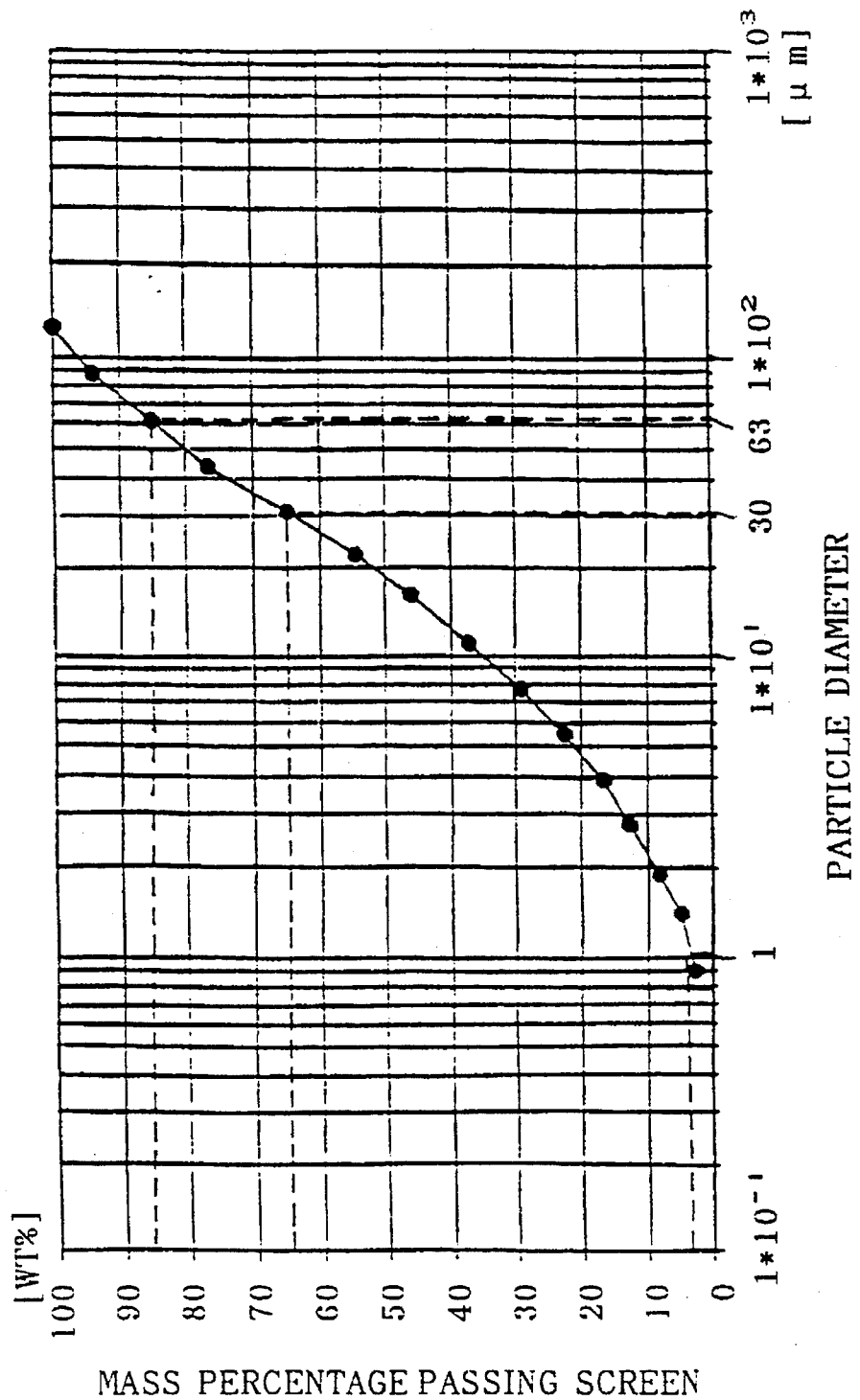
FIG. 4 is the particle size distribution of natural zeolite according to Example 1 of the invention.
Figure 5:
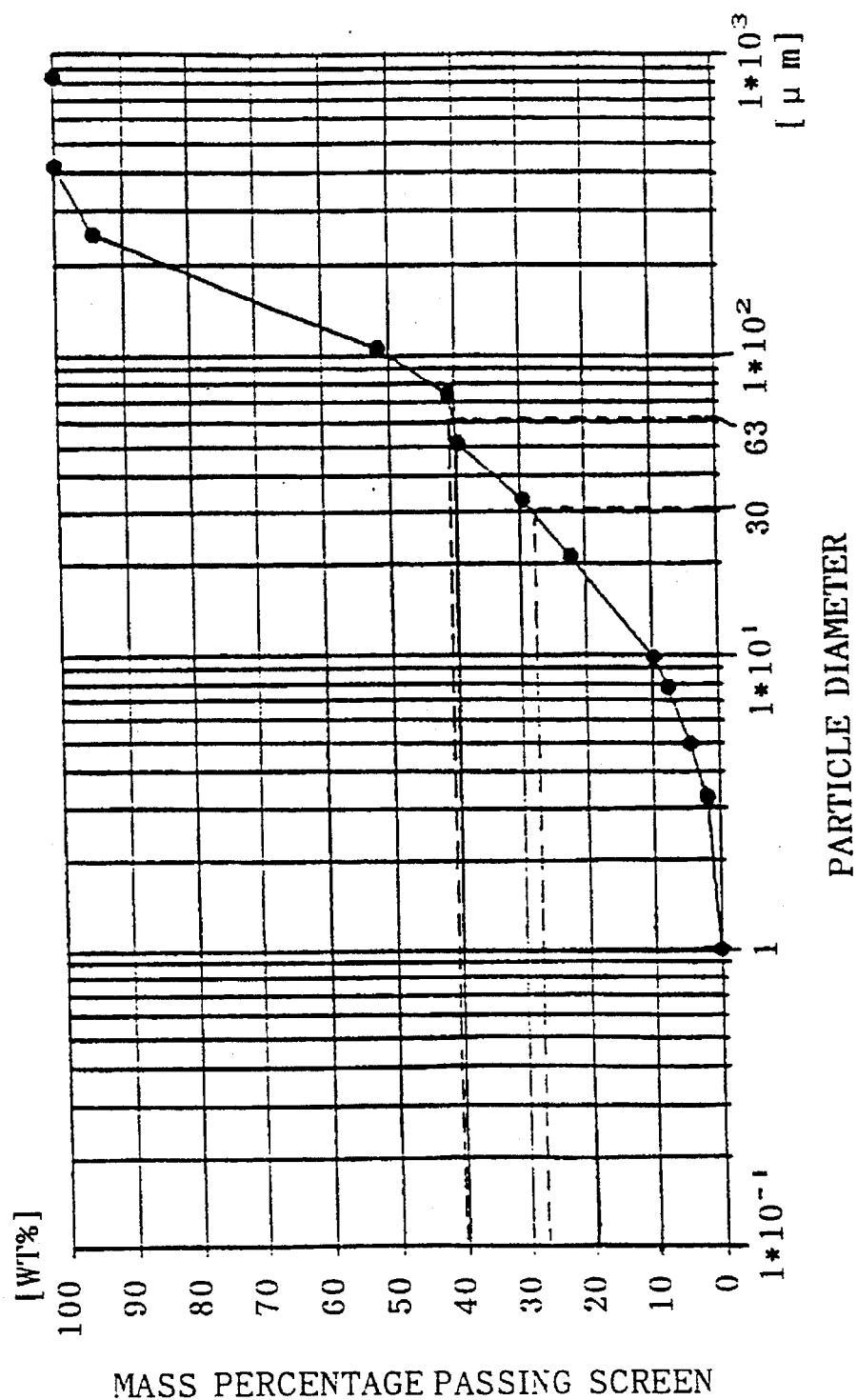
FIG. 5 is the particle size distribution of natural zeolite according to Example 2 of the invention.

FIG. 4 shows the particle size distribution of the insecticide of Example 1, and FIG. 5 shows the particle size distribution of the insecticide of Example 2, both of these insecticides consisting of powdered natural zeolite prepared as described hereintofore.

From these particle size distributions, it is seen that in the case of the insecticide of Example 1, more than 85% of the material consists of particles smaller than the distance between insect hairs, i.e. 63 μm, and is therefore able to act on the insects by the first, second and third mechanisms. Of this proportion, approximately 65% acts according to the second mechanism corresponding to the aforementioned particles 82, 83. The remaining proportion, which is inactive and amounts to only slightly less than 15%, has the sole function of reducing humidity in the area to which the insecticide is applied.

In the case of the insecticide of Example 2, approximately 40% of the material by weight acts on the insects by the first, second and third mechanisms. Of this proportion, more than 25% acts by the second mechanism corresponding to the aforementioned particles 82, 83. The remaining proportion, which is inactive, is as high as approximately 60%.

The results of confirmatory tests using these insecticides consisting of powdered natural zeolite, will now be given. First, the case of the natural zeolite of Example 1 will be described.

Ten termites were placed in a Petri dish containing the aforesaid natural zeolite insecticide of Example 1.

After 1 hour, all ten termites were alive with insecticide adhering to their body. Eight termites were moving around, and the remaining two were waving their legs and feelers.

After 2 hours, four termites had died, and the remaining six were merely waving their legs and feelers occasionally.

After 3 hours, nine termites had died, and the remaining termite was waving its legs and feelers.

After 4 hours, nine insects had died, and the remaining termite was twitching its legs.

After 5 hours, all ten termites had died, and the test was terminated.

Next, the case of the natural zeolite of Example 2 will be described.

Ten termites were placed in a Petri dish containing the aforesaid natural zeolite insecticide of Example 2.

After 1 hour, all ten termites were alive with insecticide adhering to their body. Five termites were moving around, and the remaining five were waving their legs and feelers.

After 2 hours, nine termites had died, and the remaining termite was twitching its legs.

After 3 hours, the remaining termite had also died.

When the dead termites from the tests of Examples 1 and 2 were observed under a microscope, the aforesaid insecticides consisting of powdered natural zeolite were found to be adhering to the skin and stomata of each insect. It may be conjectured that the aforesaid first, second and third mechanisms had combined to cause the death of the termites.

In Example 3, the insecticide consisted only of artificial zeolite. The results of a confirmatory test of the activity of this insecticide will now be described.

The artificial zeolite used as an insecticide in Example 3 was coal ash zeolite manufactured by Nippon Steel Ltd., which was crushed to a powder. The ion exchange capacity of this insecticide was 200–350 meq/100 g. Table 1 shows its chemical composition.

Figure 6:
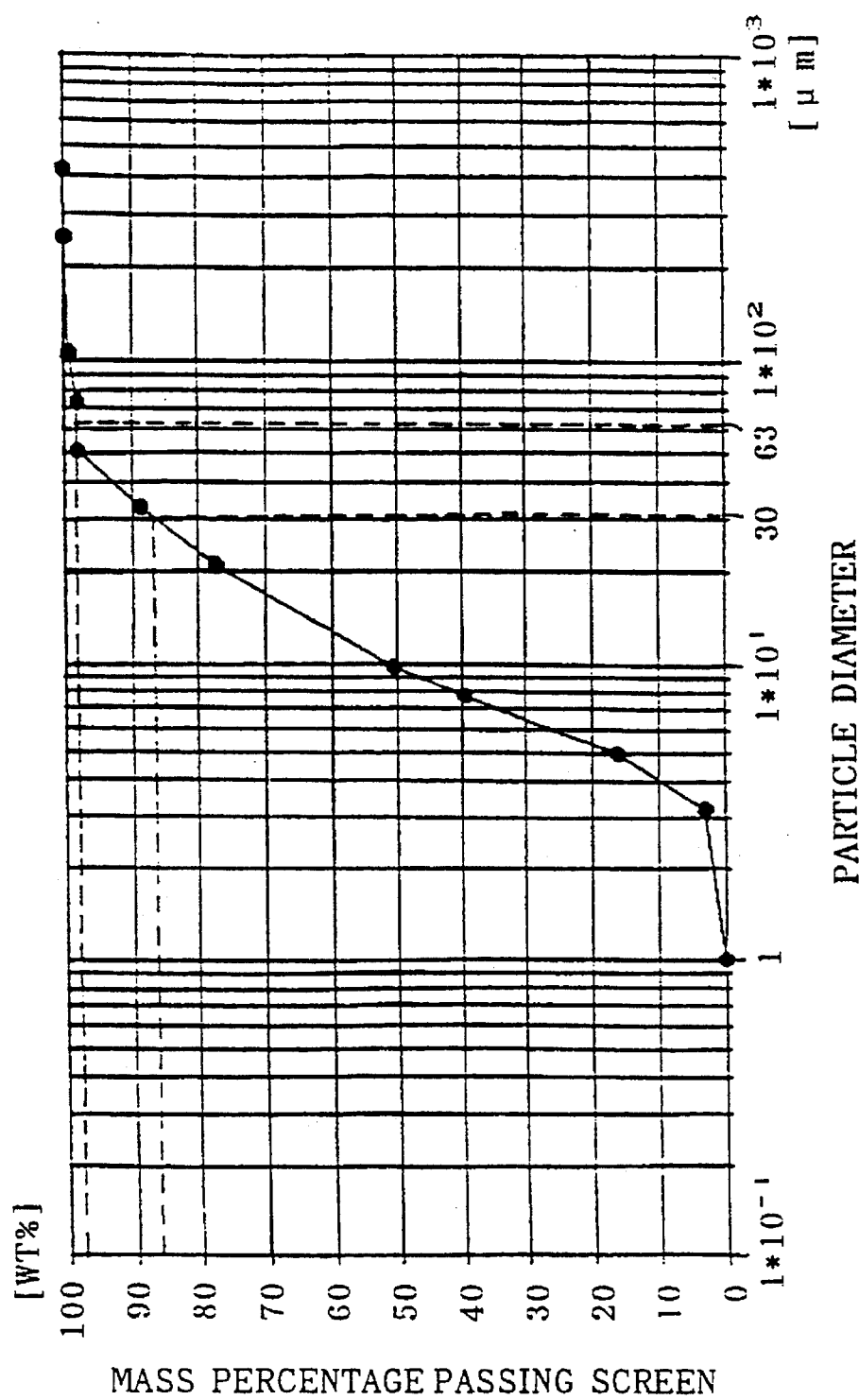
FIG. 6 is the particle size distribution of artificial zeolite according to Example 3 of the invention.

FIG. 6 shows the particle size distribution of the insecticide of Example 3. More than 95% of the material acts on the insects by the first, second and third mechanisms. Of this proportion, more than 85% acts by the second mechanism corresponding to the aforementioned particles 82, 83.

The confirmatory test of this insecticide consisting of powdered artificial zeolite was performed as described hereintofore.

Ten termites were placed in a Petri dish containing the aforesaid powdered synthetic zeolite.

After 1 hour, all ten termites were alive with insecticide adhering to their body. Eight termites were moving around, and the remaining two were waving their legs and feelers.

After 2 hours, one termite had died. A further six were still moving round, but three were merely twitching their legs and feelers.

After 3 hours, two termites had died. A further seven were waving their legs and feelers, and the remaining one was moving slowly.

After 4 hours, seven termites had died, and the remaining three were waving their legs and feelers.

After 5 hours, nine termites had died, and the remaining one was waving its legs. As it was clear that the aforesaid insecticide consisting of powdered artificial zeolite had insecticidal activity, the test was terminated at this point.

When the dead termites from this confirmatory test were observed under a microscope, powdered insecticide was found to be adhering to the skin of the insects including the stomata as in the case of the insecticide consisting of natural zeolite.

It may therefore be conjectured that, in the case of not only natural zeolite but also artificial zeolite, the aforesaid first, second and third mechanisms combine together to act on the insects. It may further be conjectured that this insecticidal action is not limited to coal ash zeolite, but extends also to artificial zeolite manufactured from volcanic ash, artificial zeolite manufactured from blast furnace slag, and synthetic zeolite manufactured chemically.

The aforesaid first, second and third mechanisms which were confirmed with powdered natural and artificial zeolite in the case of termites, are physical effects depending on the relation of the particle diameters of the zeolite insecticide to the distance P between the body hairs 3 and the opening W of the stoma 6 of the insect 1 which it is desired to eliminate. The insecticide may therefore be used on a variety of harmful insects.

Insects which can be eliminated using the insecticide of the present invention include, for example, other types of termites or houseticks, house dust mites, acarid mites and cockroaches, as well as mosquitoes, flies, fleas, sucking lice, powderpost beetles, deathwatch and drugstore beetles, Indian meal moths, sawtoothed grain beetles, red flour beetles, maize weevils, azuki bean weevils, varied carpet beetles, black carpet beetles, casemaking clothes moths, midges, moth flies and sand flies, stink bugs, horse flies, mites, stable flies, Asiatic stem borers, planthoppers, green rice leafhoppers, soybean beetles, limabean pod borers, fruit borers, sacle insects, spider mites, aphids, diamondback moths, cabbage armyworms, vegetable weevils, Japanese pine sawyers, bark beetles, chafers, lawn grass cutworms and bluegrass webworms.

Of the aforesaid types of insects, houseticks such as dust mites and acarid mites possess no stomata and take in oxygen through the skin 2. The insecticide of the present invention therefore does not act by the aforesaid second mechanism. Natural zeolite adhering to the insect's skin however eliminates insects not only by preventing carbon dioxide release but also by obstructing oxygen intake according to the aforesaid first mechanism. In addition, it definitively eliminates insects by its dehydrating action on body scratches according to the aforesaid third mechanism.

It is clear from the aforesaid description of the first, second and third mechanisms that the particle diameters of the active components of the insecticide are determined by the distance P between the body hairs and other features of the insect which it is desired to eliminate. If this insect is different from a termite, therefore, it is to be preferred that the particle size distribution of the insecticide used is suitably adjusted. In the case of an insecticide intended for a specific type of insect, moreover, it is effective to separate particles having a diameter smaller than the distance P between body hairs of the insect, and use only these particles as the insecticide.

For example, in the case of a cheyletid, which is a type of housetick, the distance between body hairs is approximately 30 μm.

If the insecticide of Example 1 (having the particle size distribution of FIG. 4) is used to eliminate these cheyletids, more than about 65% by weight of the material functions as an active component which can reach the tick's skin.

As the opening W of the tick's stomata is approximately 1 μm, the proportion of the material which functions like the insecticide particles 82, 83 according to the aforesaid second mechanism, is a little less than 5% by weight.

In such a case, the particle size distribution of the insecticide should be adjusted so that there are many fine particles. Further, if particles having a diameter larger than the distance P between the body hairs 3 of the insect, i.e. 30 μm, are removed, there is a higher probability that the insecticide will adhere to the tick's skin, and the action of the insecticide will be enhanced.

If harmful insects are eliminated by zeolite which was confirmed to have an insecticidal action as described hereintofore, either natural zeolite or artificial zeolite may be used alone as in the aforesaid examples. It is however practical to use mixtures of these with suitable amounts of other solids such as fillers or enhancers which enhance insecticidal activity.

From this viewpoint, the inventors performed tests using various other solid substances. In the following examples, insecticidal activity was confirmed where zeolite was used in admixture with the solid substances mentioned hereinafter.

The results of these confirmatory tests will now be described. The zeolite used in these tests was identical to that used in Example 1, and the test method was the same.

In Example 4, the insecticide was a mixture wherein talc, a clay mineral, was added to the aforesaid natural zeolite. The blending proportion by weight was zeolite 90%, talc 10%.

Talc is a type of magnesium clay having the chemical formula:

$$Mg_3Si_4O_{10}(OH)_2.$$

Figure 7:
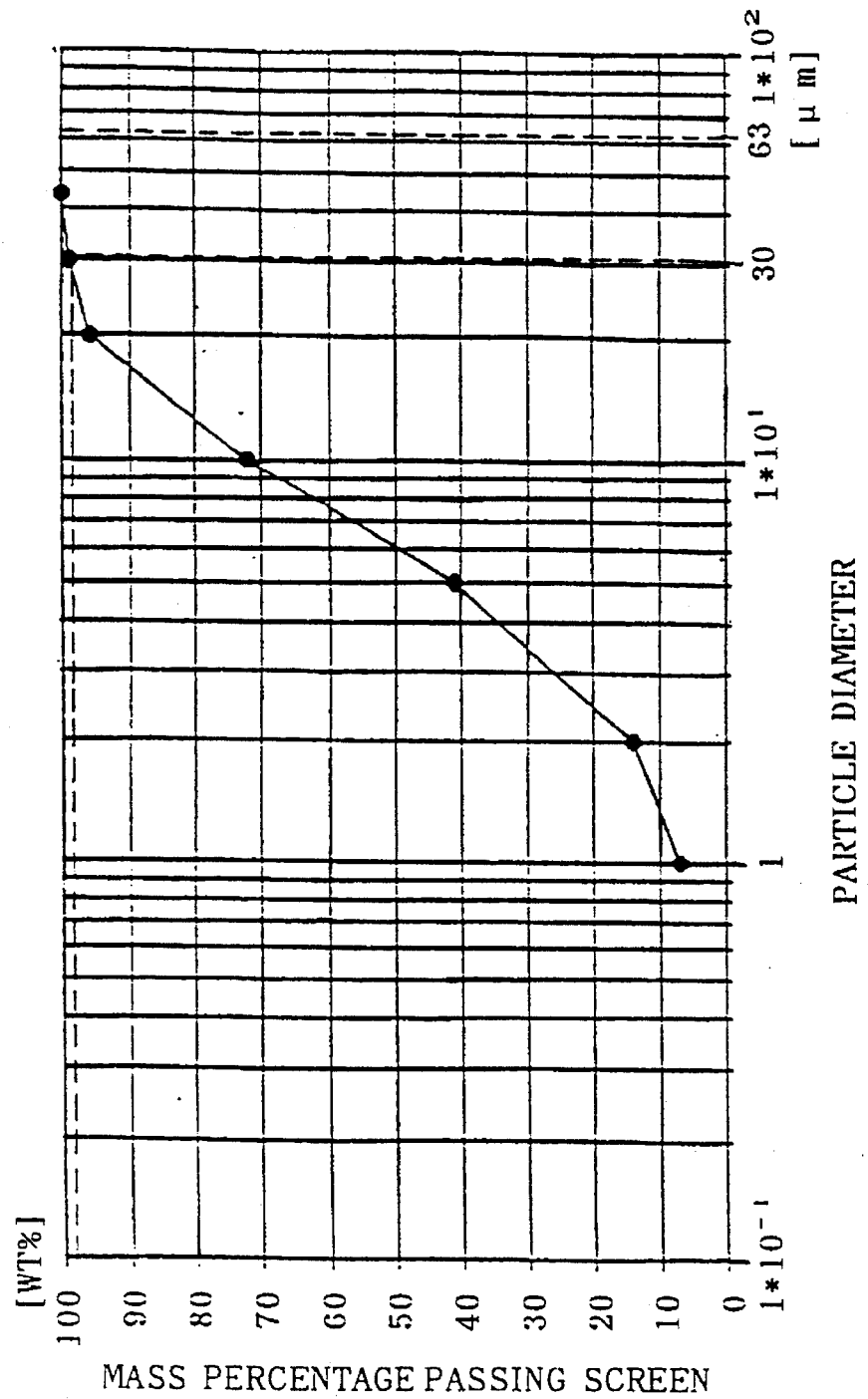
FIG. 7 is the particle size distribution of talc used in Example 4 of the invention.

The talc used in the test was "3S Talc" (commercial name) manufactured by Maruo Calcium Ltd., and its particle size distribution is given in FIG. 7. As is clear from FIG. 7, all of the talc consists of particle diameters which are active against termites.

Ten termites were placed in a Petri dish containing the aforesaid insecticide of Example 4.

After 1 hour, one of the termites had died. The remaining nine termites, which had insecticide adhering to their body, were merely waving their legs and feelers occasionally.

After 2 hours, nine termites had died, and the remaining termite was twitching its legs.

After 3 hours, the remaining termite had died.

When the dead termites from this confirmatory test were observed under a microscope, powdered insecticide was found to be adhering to the skin of the insects including the stomata as in the case of Example 1. This confirmed that the insecticidal mechanism was the same as that of Example 1.

The inventors performed similar confirmatory tests on mixtures wherein clay minerals other than talc, i.e. clay, bentonite or sepiolite, were added in powder form to the aforesaid natural zeolite, but the details of these tests will be omitted here.

Clay is an agglomeration of fine particles formed by the decomposition or breakdown of minerals in rock. Bentonite is a type of clay mineral of which the principal components are montmorillonite and beidellite, and which is also referred to as swelling soil. Sepiolite is a type of magnesium clay of which the chemical composition is represented by the formula:

$$Mg_9Si_{12}O_{30}(OH)_6(OH_2)_4.6H_2O.$$

It was confirmed that when these clays were used, insecticidal activity was present in every case. It thus appears that clays generally possess insecticidal activity in admixture with zeolite.

In Example 5, the insecticide was a mixture wherein diatomaceous earth was added to the aforesaid natural zeolite. The blending proportion by weight was zeolite 50%, diatomaceous earth 50%.

Diatomaceous earth is a siliceous sedimentary rock formed for example by deposition of skeletal remains of diatoms on the seabed, and it also contains clay, volcanic ash and organic matter.

Figure 8:
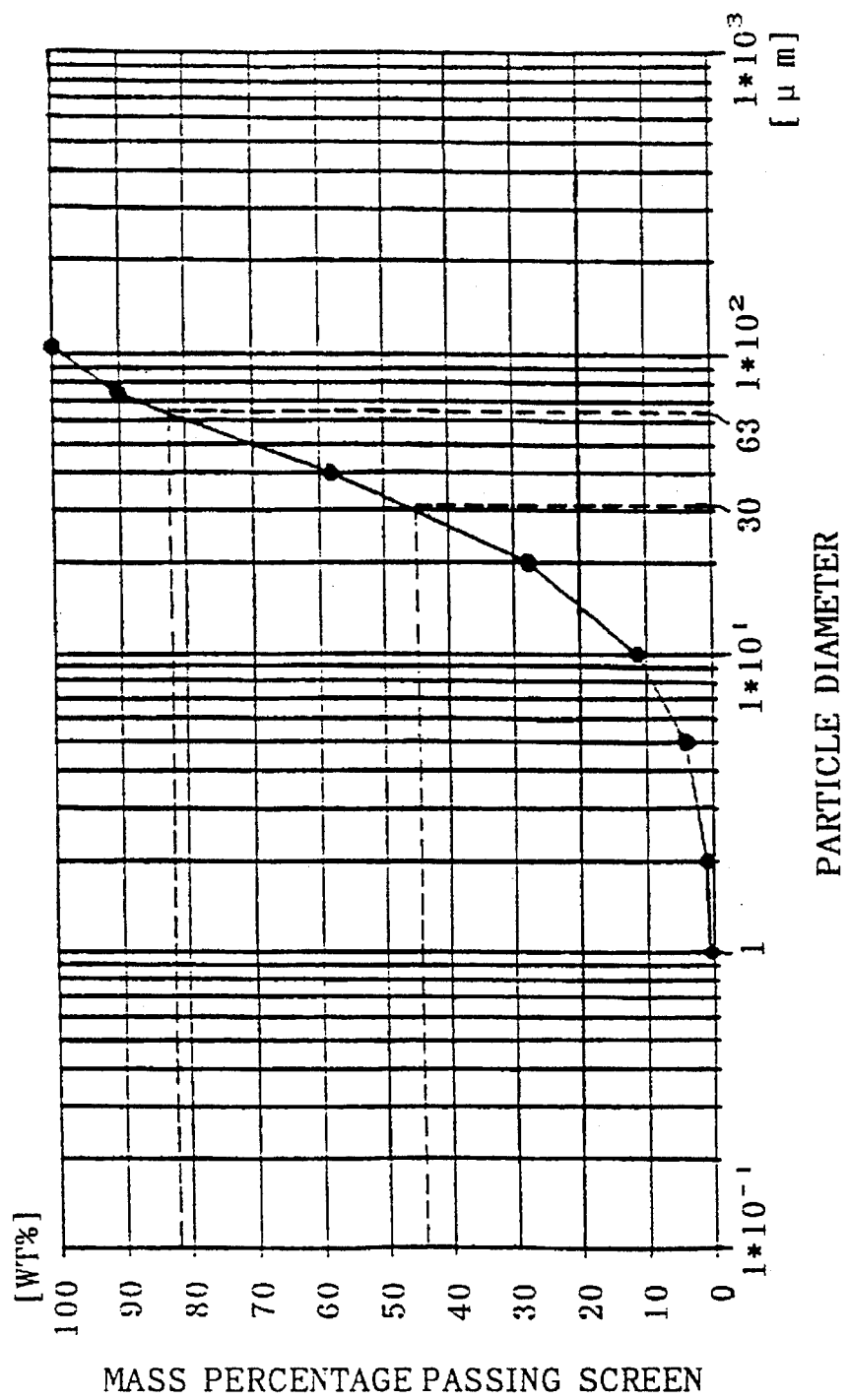
FIG. 8 is the particle size distribution of diatomaceous earth used in Example 5 of the invention.

The diatomaceous earth used in the test was "Radiolite #500" (commercial name) manufactured by Showa Chemicals Ltd., and its particle size distribution is given in FIG. 8. As is clear from FIG. 8, more than approximately 80% of this diatomaceous earth consists of particle diameters which are active against termites.

Ten termites were placed in a Petri dish containing the aforesaid insecticide of Example 5.

After 1 hour, all ten termites were alive with insecticide adhering to their body. Eight termites were moving around, and the remaining two were waving their legs and feelers.

After 2 hours, all ten termites were still alive with insecticide adhering to their body. Eight termites were were still moving round, and of the remaining two, one was waving its legs and feelers while the other was merely twitching its legs occasionally.

After 3 hours, all ten termites were still alive. Six termites were moving around, and the remaining four were merely moving their legs and feelers slightly.

After 4 hours, six termites had died, and of the remaining four, two were moving around while the other two were merely moving their legs and feelers occasionally.

After 5 hours, nine termites had died, and the remaining one was merely moving its legs and feelers occasionally. As it was clear that the insecticide of Example 5 had insecticidal activity, the test was terminated at this point.

When the dead termites from this confirmatory test were observed under a microscope, powdered insecticide was found to be adhering to the skin of the insects including the stomata as in the case of Example 1. This confirms that the mechanism of the insecticide was the same as that of Example 1.

In Example 6, the insecticide was a mixture wherein volcanic ash was added to the aforesaid natural zeolite. The blending proportion by weight was zeolite 90%, volcanic ash 10%.

Figure 9:
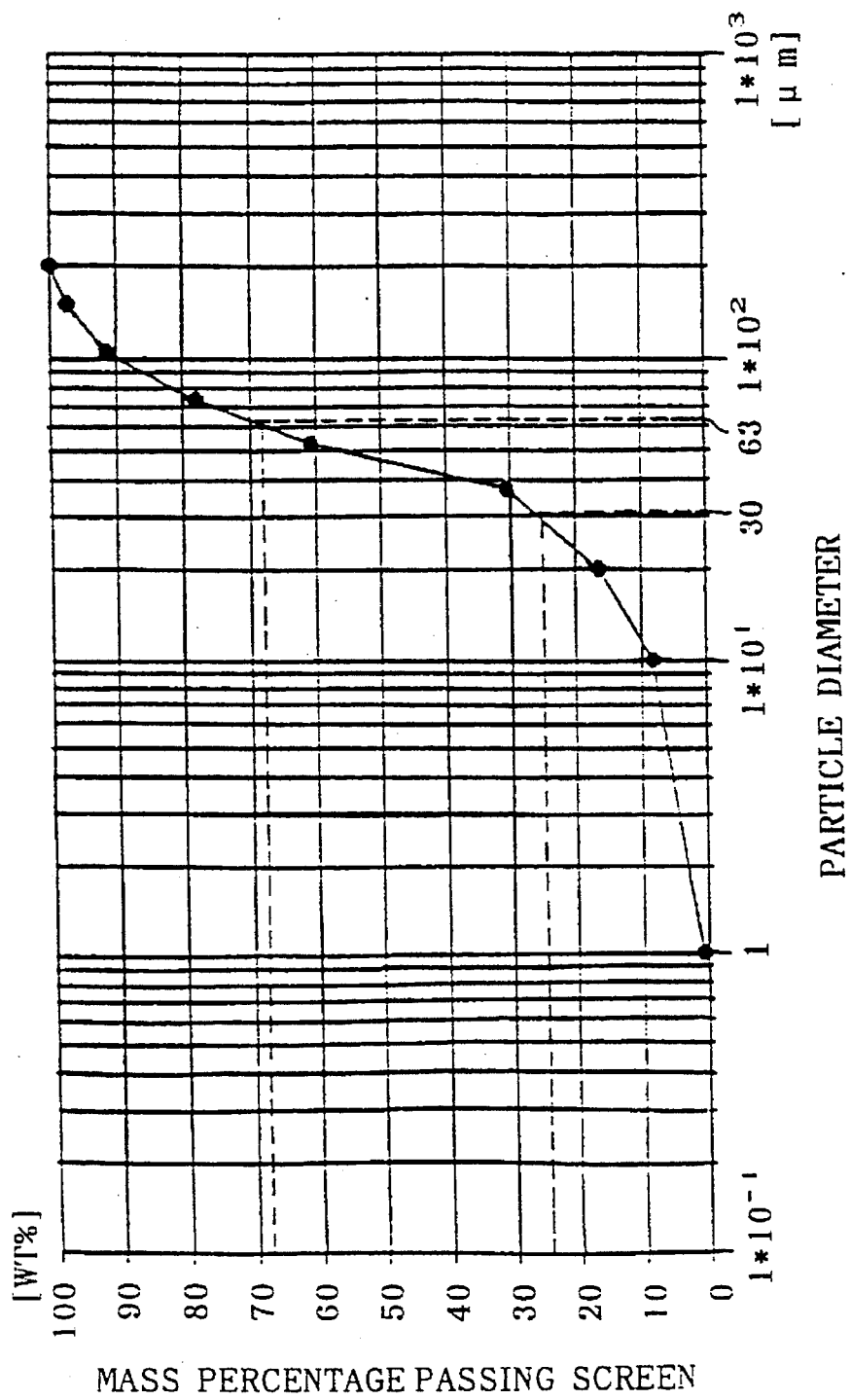
FIG. 9 is the particle size distribution of volcanic ash used in Example 6 of the invention.

Volcanic ash is the general name for a pumice type of volcanic ash deposit. The volcanic ash used in the test was "S-20" (commercial name) manufactured by Ijichi Chemicals Ltd., and its particle size distribution is given in FIG. 9. As is clear from FIG. 9, a little less than 70% of this volcanic ash consists of particle diameters which are active against termites.

Ten termites were placed in a Petri dish containing the aforesaid insecticide of Example 6.

After 1 hour, all ten termites were alive with insecticide adhering to their body. Eight termites were moving around, and the remaining two were waving their legs and feelers.

After 2 hours, four termites had died and the remaining six were merely moving their legs and feelers occasionally.

After 3 hours, all ten termites had died, and the test was terminated.

When the dead termites from the test of Example 6 were observed under a microscope, powdered insecticide was found to be adhering to the skin of the insects including the stomata as in the case of Example 1. This confirms that the mechanism of the insecticide was the same as that of Example 1.

In Example 7, the insecticide was a mixture wherein calcium carbonate ($CaCO_3$) was added to the aforesaid natural zeolite. The blending proportion by weight was zeolite 50%, calcium carbonate 50%.

Figure 10:
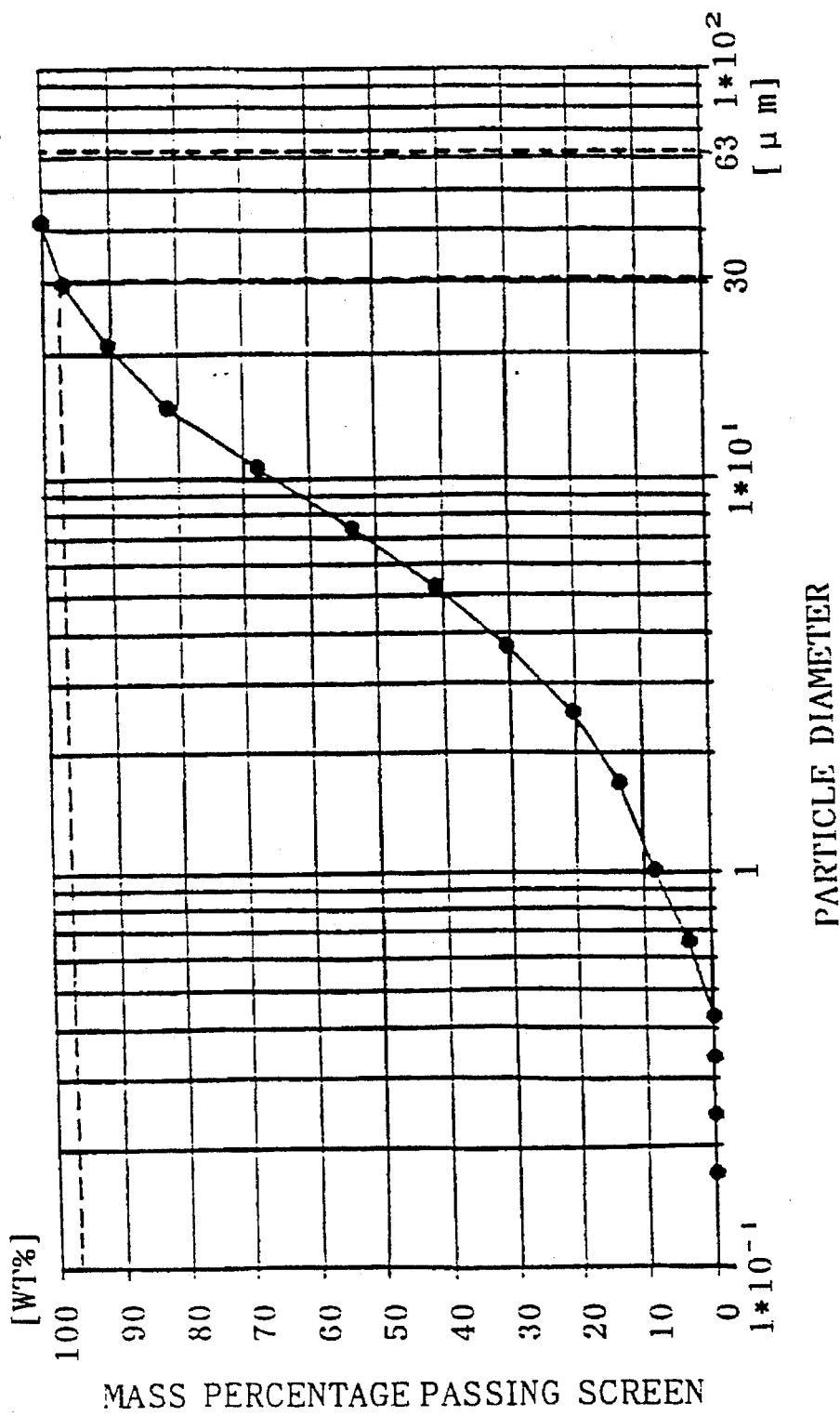
FIG. 10 is the particle size distribution of calcium carbonate used in Example 7 of the invention.

This calcium carbonate was "Special Lice S" (commercial name) manufactured by Maruo Calcium Ltd., and its particle size distribution is given in FIG. 10. As is clear from FIG.

10, all of the calcium carbonate consists of particle diameters which are active against termites.

Ten termites were placed in a Petri dish containing the aforesaid insecticide of Example 7.

After 1 hour, all ten termites had insecticide adhering to their body. One termite had died, and the remaining nine were waving their legs and feelers.

After 2 hours, all ten termites had died and the test was terminated.

When the dead termites from the test of Example 7 were observed under a microscope, powdered insecticide was found to be adhering to the skin of the insects including the stomata as in the case of Example 1. This confirms that the mechanism of the insecticide was the same as that of Example 1.

In an Example 8, the insecticide was a mixture wherein coal ash was added to the aforesaid natural zeolite. The blending proportion by weight was zeolite 50%, coal ash 50%.

Figure 11:
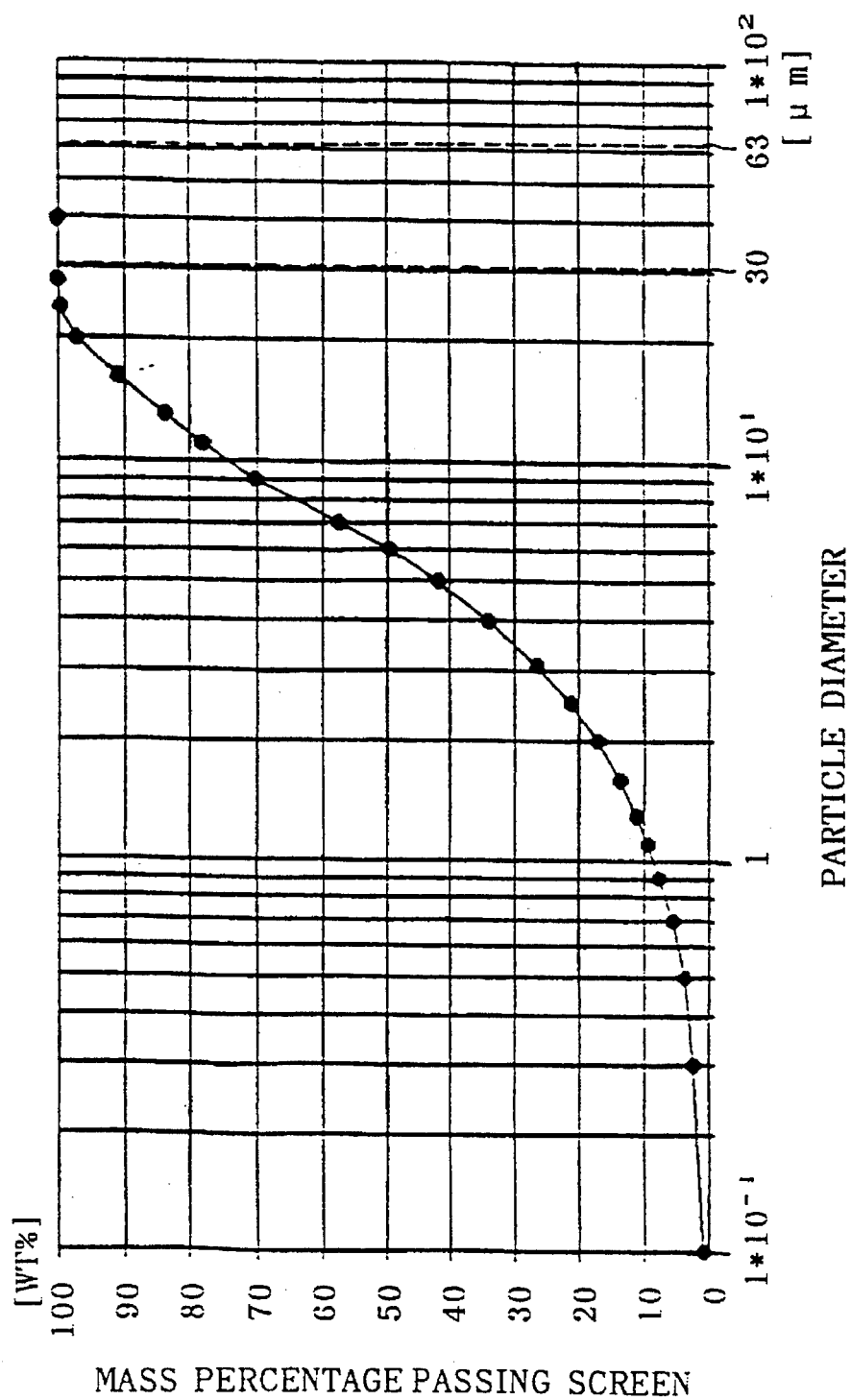
FIG. 11 is the particle size distribution of coal ash used in Example 8 of the invention.

Coal ash is an ash recovered from flue gases such as are discharged by boilers which use powdered coal. The coal ash used in the test was "ONODA SUPER FLOW" (commercial name) manufactured by Onoda Cement Ltd., and its particle size distribution is given in FIG. 11. As is clear from FIG. 11, all of the coal ash consists of particle diameters which are active against termites.

Ten termites were placed in a Petri dish containing the aforesaid insecticide of Example 8.

After 1 hour, all ten termites were alive with insecticide adhering to their body. Eight termites were moving around, and the remaining two were waving their legs and feelers.

After 2 hours, two of the termites had died. Of the remainder, one was moving around and seven were merely moving their legs and feelers occasionally.

After 3 hours, six termites had died. The remaining four were merely moving their legs and feelers slightly.

After 4 hours, all of the termites had died, and the the test was terminated.

When the dead termites from the test of Example 8 were observed under a microscope, powdered insecticide was found to be adhering to the skin of the insects including the stomata as in the case of Example 1. This confirms that the mechanism of the insecticide was the same as that of Example 1.

In an Example 9, the insecticide was a mixture wherein silica gel was added to the aforesaid natural zeolite. The blending proportion by weight was zeolite 50%, silica gel 50%.

Figure 12:
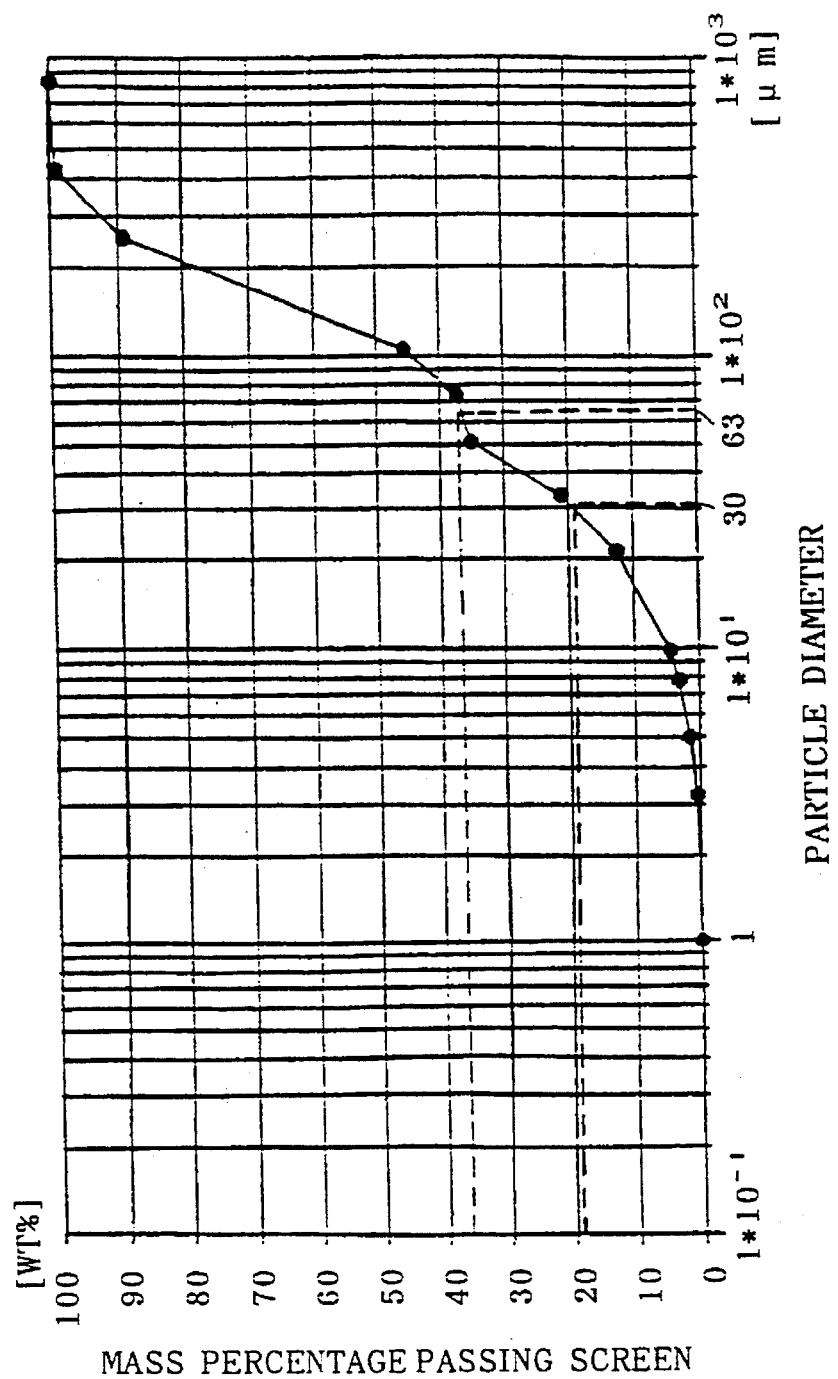
FIG. 12 is the particle size distribution of silica gel used in Example 9 of the invention.

The silica gel used in the test was "Fuji Home Gel G" (commercial name) manufactured Fuji Davison Chemicals Ltd., and its particle size distribution is given in FIG. 12. As is clear from FIG. 12, more than approximately 35% of this silica gel consists of particle diameters which are active against termites by means of the aforesaid mechanisms, the remaining larger proportion having the function of maintaining dry conditions in the Petri dish.

Ten termites were placed in a Petri dish containing the aforesaid insecticide of Example 9.

After 1 hour, all ten termites were alive but they had insecticide adhering to their body, and were merely moving their legs and feelers slightly.

After 2 hours, all ten termites has died and the test was terminated.

When the dead termites from this confirmatory test were observed under a microscope, powdered insecticide was found to be adhering to the skin of the insects including the stomata as in the case of Example 1. This confirms that the mechanism of the insecticide was the same as that of Example 1. There were also characteristic black areas on the bodies of the termites which are probably due to the action of the silica gel.

In an Example 10, the insecticide was a mixture wherein silicic acid anhydride ($SiO_2$) was added to the aforesaid natural zeolite. The blending proportion by weight was zeolite 50%, silicic acid anhydride 50%.

The silicic acid anhydride used in the test was "Raolosil QS-102" (commercial name) manufactured by Tokuyama Soda Ltd. Its particle size distribution lies approximately in the range 75 m$\mu$–275 m$\mu$, i.e. far smaller than the particle diameters which are active by means of the aforesaid first, second and third mechanisms.

Ten termites were placed in a Petri dish containing the aforesaid insecticide of Example 10.

After 1 hour, all ten termites had insecticide adhering to their body and three had died. Of the remaining seven, two were waving their legs and feelers, and five were merely twitching them occasionally.

After 2 hours, all ten termites had died and the test was terminated.

When the dead termites from this confirmatory test were observed under a microscope, powdered insecticide was found to be adhering to the skin of the insects including the stomata as in the case of Example 1. This confirms that the mechanism of the insecticide was the same as that of Example 1.

In the aforesaid examples, insecticides have been described wherein natural zeolite, artificial zeolite or synthetic zeolite were used alone or in admixture with suitable solids. This patent application is however not limited to these cases, and chemicals having weak insecticidal activity such as for example boric acid may also be added. Further, it will be understood that the blending proportion of such added solids may be suitably adjusted, and two or more solids may be used in conjunction as may be desired.

As described hereintofore, the insecticide of the present invention employs zeolite with the addition of suitable solids or other weakly active chemicals. As it is not as strong as conventional insecticides, it is does not require as much care in handling as for example when the insecticide is sprayed, and it is moreover easy to use.

ADVANTAGES OF INVENTION

As described hereintofore, in the insecticide provided, the zeolite has moisture regulating properties, and can therefore maintain dry conditions unsuitable for sustaining harmful insects in areas where the insecticide is used.

In areas to which this insecticide is applied, therefore, harmful insects are not easily sustained, the number of harmful insects decreases, and even if some harmful insects still remain, they are far less active.

As the aforesaid zeolite contains some particles having a diameter smaller than the distance between insect body hairs, a fine powder of these particles adheres to the insect's body surface despite the presence of the hairs. This prevents release of carbon dioxide gas from the insect's skin, and causes the insect's death due to respiratory failure.

If the harmful insect which it is desired to eliminate has stomata, the aforesaid fine zeolite powder adheres to the stomata. This prevents the insect from taking in oxygen, and causes the insect's death due to oxygen deficiency.

Further, when foreign matter adheres to an insect's the body surface or hairs, the insect tries to brush it off. In this brushing off action, the insect scratches itself. The aforesaid fine powder then adheres to the scratches despite the presence of body hairs, and due to the moisture regulating properties of the zeolite, the zeolite absorbs the insect's body fluids which causes the insect's death by dehydration.

This type of zeolite is not only less toxic than conventional insecticides, but it also effective as an insecticide due to the aforesaid mechanisms.

The insecticide provided by the invention therefore has little adverse effect on man or animals and presents little risk of environmental pollution, but definitively eliminates harmful insects even when used over long periods of time without the insects acquiring resistance.

What is claimed is:

1. A dry insecticide for termites, consisting essentially of:

dry powdered zeolite particles for contacting and covering skin of a termite and preventing release of carbon dioxide gas from the skin covered by zeolite particles, said zeolite particles having a diameter of less than 63 μm, said diameter being less than the distance between body hairs of a termite, and containing at least 40% by weight of the insecticide; and dry powdered zeolite particles for covering openings of stomata of a termite and preventing intake of air by the termite, said zeolite particles having a diameter of less than 30 μm, said diameter being less than the diameter of a stoma of a termite and containing at least 25% by weight of the insecticide;

whereby the insecticide functions by failure of intake of oxygen through the stomata and failure of exit of carbon dioxide through the skin, causing death of the termite by dehydration and respiratory failure.

2. A dry insecticide, consisting essentially of dry powdered zeolite particles for contacting and covering skin of an insect and preventing release of carbon dioxide gas from the skin covered by said zeolite particles, said zeolite particles having a diameter of less than the distance between body hairs of the insect to be exterminated, and containing at least 40% by weight of the insecticide;

whereby the insecticide functions by failure of exit of carbon dioxide through the skin, causing insect death by respiratory failure.

3. An insecticide for termites as defined in claim 1, further consisting essentially of one or more powdered substances selected from the group consisting of clay mineral, diatomaceous earth, volcanic ash, calcium carbonate and fly ash, said powdered substances comprising particles having a diameter less than 63 μm which corresponds to the distance between body hairs on said termites and particles having a diameter smaller than 30 μm which corresponds to a diameter of a stoma of said termites.

4. An insecticide for termites as defined in claim 1, further consisting essentially of powdered silica gel or silicic acid anhydride, said powdered silica gel or silicic acid anhydride comprising particles having a diameter smaller than 63 μm which corresponds to the distance between body hairs on said termites and particles having a diameter smaller than 30 μm which corresponds to a diameter of a stoma of said termites.

5. An insecticide for termites as defined in claim 1, wherein said zeolite consists essentially of natural zeolite.

6. An insecticide for termites as defined in claim 1, wherein said zeolite consists essentially of artificial zeolite.

* * * * *